(12) United States Patent
Yonezawa

(10) Patent No.: US 6,621,568 B1
(45) Date of Patent: Sep. 16, 2003

(54) DEFECT INSPECTING APPARATUS

(75) Inventor: Eiji Yonezawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 258 days.

(21) Appl. No.: 09/606,169

(22) Filed: Jun. 29, 2000

(30) Foreign Application Priority Data

Jun. 30, 1999 (JP) ............................................ 11-184881

(51) Int. Cl.⁷ ..................... G01N 21/00; G01N 21/88; G01N 21/86; G06K 9/00
(52) U.S. Cl. ......................... 356/237.2; 250/559.45; 250/559.41; 382/141
(58) Field of Search ..................... 356/237.1, 237.4, 356/237.3, 237.5, 237.2; 250/559.11, 559.13, 559.45; 382/149, 147, 145, 141; 348/126, 125, 128

(56) References Cited

U.S. PATENT DOCUMENTS

| | | | |
|---|---|---|---|
| 4,618,938 A | * 10/1986 | Sandland et al. ............ 382/148 |
| 4,845,558 A | 7/1989 | Tsai et al. .................... 358/106 |
| 4,871,257 A | * 10/1989 | Suzuki et al. ............... 356/400 |
| 4,999,510 A | * 3/1991 | Hayano et al. ......... 250/559.41 |
| 5,046,847 A | * 9/1991 | Nakata et al. .......... 250/559.41 |
| 5,177,559 A | 1/1993 | Batchelder et al. ......... 356/237 |
| 5,363,187 A | * 11/1994 | Hagiwara et al. ....... 250/559.41 |
| 5,625,193 A | 4/1997 | Broude et al. |
| 5,917,588 A | * 6/1999 | Addiego ................. 356/237.2 |
| 6,167,148 A | * 12/2000 | Calitz et al. ................. 348/126 |
| 6,178,257 B1 | * 1/2001 | Alumot et al. .............. 382/145 |
| 6,263,099 B1 | * 7/2001 | Maeda et al. ............... 356/394 |

FOREIGN PATENT DOCUMENTS

| | | | |
|---|---|---|---|
| EP | 0 406 030 A2 | 1/1991 | |
| EP | 0 930 498 A2 | 7/1999 | .......... G01N 21/88 |
| JP | 5-118994 | 5/1993 | .......... G01N 21/88 |
| JP | 6-222013 | 8/1994 | .......... G01N 21/88 |
| JP | 7-27709 | 1/1995 | .......... G01N 21/88 |

* cited by examiner

Primary Examiner—Zandra V. Smith
Assistant Examiner—Gordon J Stock
(74) Attorney, Agent, or Firm—Sughrue Mion, PLLC

(57) ABSTRACT

A defect inspecting apparatus for inspecting a defect of an object having a periodic pattern includes: a dark field illumination optical system that illuminates the object with substantially parallel illumination light in a direction having a predetermined first inclined angle relative to an inspection surface of the object; an imaging optical system having an imaging element for imaging the object illuminated with the illumination light, the imaging element having an imaging lens; and a defect detecting system for detecting the defect based on image data of the object thus imaged. A mutual positional relation ship between the direction of illumination by the illumination optical system and a direction of imaging by the imaging optical system is determined based on a diffraction angle defined by a period of the pattern and a wavelength of the illumination light. A sum of an aperture angle of the illumination light and an object side aperture angle of the imaging lens is set to be smaller than the diffraction angle.

10 Claims, 8 Drawing Sheets

DEFECT INSPECTING APPARATUS

BACKGROUND OF THE INVENTION

The present invention relates to a defect inspecting apparatus for inspecting a defect on the surface of an object to be inspected, such as a semiconductor wafer.

As a method of inspecting a defect such as a scar or dust on the surface of a semiconductor wafer (hereafter also referred to as the wafer), a method is known which makes use of dark field illumination in which illuminating light is applied to the wafer surface from a diagonal direction.

By making use of this dark field illumination, a defect is conventionally inspected by an operator by rotating or tilting the wafer and by visually observing the presence of an abnormal spot. In recent years, however, to automate the inspection, a method has been proposed in which the overall wafer is imaged by a CCD camera, and its image data is subjected to image processing so as to inspect a defect.

However, since the scattered light from a defect such as a scar or dust on the basis of dark field illumination is very weak, portions other than the defect should preferably be relatively dark in performing inspection based on image processing. However, in a wafer having a very small periodic pattern formed thereon, diffracted light occurs due to the pattern, so that it is difficult to create a dark field state for inspecting the defect with high sensitivity. Further, the arrangement becomes complicated in realizing by image processing those which have been done by the operator, and there is a problem in the processing speed as well.

Further, an operation for examining and setting in advance an optimum illuminating angle is required in image processing. However, since an optimum illuminating angle differs depending on the type of wafer, much time and trouble is required to cope with a large number of types of wafer. Furthermore, in the case of a wafer having a pattern for which a sufficient dark field state cannot be obtained at whatever illuminating angles, the defect detection sensitivity becomes poor.

SUMMARY OF THE INVENTION

In view of the problems of the above-described conventional art, it is an object of the present invention to provide a defect inspecting apparatus which is capable of effecting defect inspection easily with high sensitivity without performing complicated adjustment or processing even with respect to objects to be inspected having different types of periodic patterns.

(1) A defect inspecting apparatus for inspecting a defect of an object having a periodic pattern, said apparatus comprising:

a dark field illumination optical system that illuminates the object with substantially parallel illumination light in a direction having a predetermined first inclined angle relative to an inspection surface of the object;

an imaging optical system having an imaging element for imaging the object illuminated with the illumination light, the imaging element having an imaging lens; and defect detecting means for detecting the defect based on image data of the object thus imaged;

wherein a mutual positional relationship between the direction of illumination by the illumination optical system and a direction of imaging by the imaging optical system is determined based on a diffraction angle defined by a period of the pattern and a wavelength of the illumination light; and wherein a sum of an aperture angle of the illumination light and an object side aperture angle of the imaging lens is set to be smaller than the diffraction angle.

(2) A defect inspecting apparatus of (1), wherein the imaging optical system is disposed to image the object in an angular direction falling within a diffraction angle defined between zero-order diffraction light and 1st-order diffraction light both being caused due to presence of the pattern.

(3) A defect inspecting apparatus of (1), wherein the imaging optical system is disposed to image the object in an angular direction located substantially at a middle of a diffraction angle defined between zero-order diffraction light and 1st-order diffraction light both being caused due to presence of the pattern.

(4) A defect inspecting apparatus of (2), wherein the illumination optical system is disposed to emit the illumination light in the direction that has the predetermined first inclined angle relative to the inspection surface of the object and that perpendicularly intersects a periodic direction of the pattern.

(5) A defect inspecting apparatus of (2), wherein:

the imaging optical system is disposed to image the object in a direction substantially perpendicular to the inspection surface of the object; and the illumination optical system is disposed to emit the illumination light in the direction that has the predetermined first inclined angle relative to the inspection surface of the object and that has a predetermined second inclined angle relative to a direction perpendicularly intersecting a periodic direction of the pattern.

(6) A defect inspecting apparatus of (5), wherein the second inclined angle is substantially identical to an angle defined between a direction of the zero-order diffraction light or the 1st order diffraction light and the imaging direction.

(7) A defect inspecting apparatus of (1), wherein the mutual positional relationship between the illuminating direction and the imaging direction is determined based on a diffraction angle defined by a maximum period of the pattern and a minimum wavelength of the illumination light.

(8) A defect inspecting apparatus of (1), further comprising:

means for mutually varying the illuminating direction relative to the object;

image preparing means for extracting pixel data of a smallest luminance from data of positionally identical pixels on images of the object taken each time when the illuminating direction is varied, and preparing image data of the object from the extracted pixel data, wherein the defect detecting means detects the defect based on the thus prepared image data.

(9) A defect inspecting apparatus of (8), wherein the varying means includes rotating means for rotating the dark field illumination optical system relative to the object.

(10) A defect inspecting apparatus of (8), wherein the varying means includes rotating means for rotating the object and the imaging optical system.

(11) A defect inspecting apparatus of (8), wherein the dark filed illumination optical system or the imaging optical system has means for setting a wavelength band to a narrow band.

(12) A defect inspecting apparatus for inspecting a defect of an object having a periodic pattern, said apparatus comprising:

a dark field illumination optical system that illuminates the object with substantially parallel illumination light in a direction having a predetermined inclined angle relative to an inspection surface of the object;

an imaging optical system having an imaging element for imaging the object illuminated with the illumination light, the imaging element having an imaging lens;

means for mutually varying the illuminating direction relative to the object;

image preparing means for extracting pixel data of a smallest luminance from data of positionally identical pixels on images of the object taken each time when the illuminating direction is varied, and preparing image data of the object from the extracted pixel data, defect detecting means for detecting the defect based on the thus prepared image data;

wherein a sum of an aperture angle of the illumination light and an object side aperture angle of the imaging lens is set to be smaller than a diffraction angle defined by a period of the pattern and a wavelength of the illumination light.

(13) A defect inspecting apparatus of (12), wherein the varying means includes rotating means for rotating the dark field illumination optical system relative to the object.

(14) A defect inspecting apparatus of (12), wherein the varying means includes rotating means for rotating the object and the imaging optical system.

(15) A defect inspecting apparatus of (12), wherein the dark filed illumination optical system or the imaging optical system has means for setting a wavelength band to a narrow band.

The present disclosure relates to the subject matter contained in Japanese patent application No. Hei. 11-184881 (filed on Jun. 30, 1999), which is expressly incorporated herein by reference in its entirety.

DESCRIPTION OF THE PREFERRED EMBODIMENT

Figure 1:
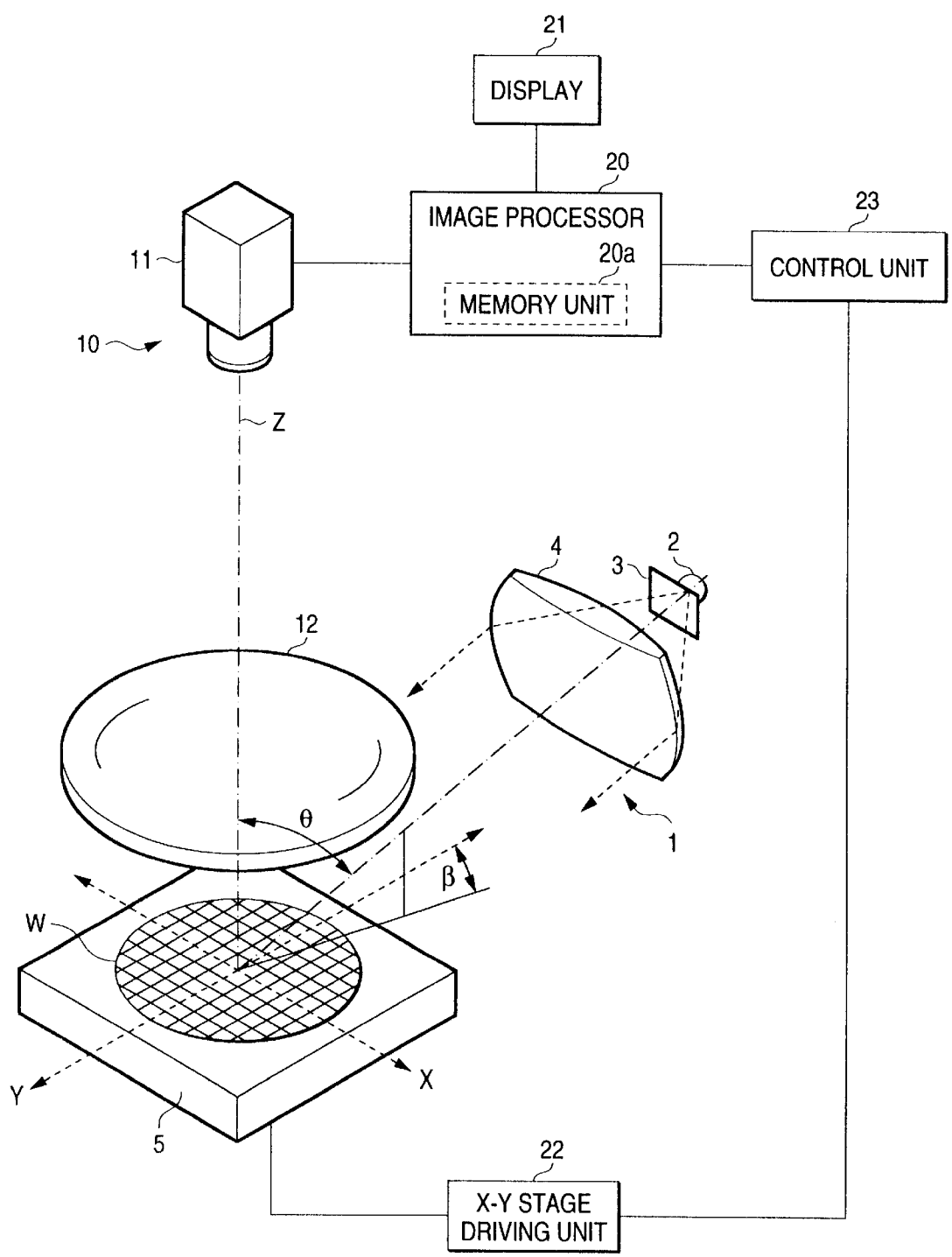
FIG. 1 is a diagram illustrating the configuration of a defect inspecting apparatus in accordance with the invention.

Referring now to the drawings, a description will be given of an embodiment of the invention. FIG. 1 is a diagram illustrating the configuration of a defect inspecting apparatus in accordance with the invention.

Reference numeral 1 denotes an optical system for dark field illumination. The illuminating light emitted from an illuminant 2, such as a halogen lamp, is converted to parallel rays of light by a lens 4, and is applied to the surface of a wafer W, i.e., an object to be inspected placed on an X-Y stage 5, from a diagonal direction. An imaging optical system 10 having a CCD camera 11 is disposed above the wafer W. A lens 12 for imaging a substantially entire area of the wafer W substantially uniformly is disposed between the camera 11 and the wafer W. The camera 11 is disposed in the vicinity of the focal position of the lens 12.

It should be noted that a narrow-band pass filter 3 for converting the band of the illuminating light to a narrow band is provided on the optical path of the optical system 1 for dark field illumination. The band for a picked-up image can be similarly made narrow if the filter 3 is provided in front of the camera 11 on the imaging optical system 10 side.

Reference numeral 20 denotes an image processor which fetches an image signal from the camera 11 after subjecting it to predetermined processing such as A/D conversion and the like, and then effects necessary preprocessing such as the correction of the sensitivity of the imaging device of the camera 11 so as to detect a defect. Numeral 20a denotes a memory of the image processor 20. Numeral 21 denotes a display on which the image fetched into the image processor 20 is displayed. Numeral 22 denotes a drive unit for driving the X-Y stage 5, and numeral 23 denotes a control unit for controlling the overall defect inspecting apparatus.

Next, a description will be given of the layout of the optical system 1 for dark field illumination and the imaging optical system 10 for obtain a satisfactory dark field image. First, a description will be given of the layout of the optical system 1 for dark field illumination for minimizing the total quantity of scattered light due to the pattern of the wafer W.

When inspecting a defect by making use of dark field illumination, in a case where a fine pattern (herein referred to as a fine pattern up to several times as large as the wavelength of illumination used as in the case of a memory pattern) is present as in the case of a semiconductor wafer, diffracted light occurs at a high level due to the scattered light based on the pattern. Therefore, the detection sensitivity is affected by the quantity of this scattered light. Since the total quantity of scattered light due to the pattern is determined by the quantity of illuminating light incident upon the wafer surface, if the angle of incidence of the illuminating light (the angle of the light with respect to the vertical direction of the wafer surface) is made large, it becomes possible to reduce the scattered light due to the pattern. Meanwhile, the scattered light from dust or the like (a defect having a projection) attached to the wafer surface does not change much even if the angle of incidence of the illuminating light is changed. Accordingly, if the angle of incidence of the illuminating light is increased, the quantity of scattered light due to dust or the like becomes large relative to the quantity of scattered light from the other portions, thereby making it possible to increase the detection sensitivity.

If the angle of incidence $\theta$ of the illuminating light upon the wafer surface is set to a maximum 90 degrees, the illuminating light travels parallel to the wafer surface, so that the scattered light due to the pattern becomes θ, and the detection sensitivity is considered to become highest. However, since the wafer surface in the manufacturing process generally has a slight warp, there are cases where the detection of a defect becomes impossible with the illumination at an angle of incidence θ=90 degrees. Meanwhile, the scattered light due to a scar (defect not having a projection) or the like decreases simultaneously with a decrease of the scattered light due to the pattern.

Accordingly, this angle of incidence is set to an angle of high efficiency so as to enhance the detection sensitivity. For practical purposes, it can be said that the angle of incidence is sufficient at θ=85 degrees or thereabouts. If a setting is provided such that θ=85 degrees, the total quantity of light incident upon the wafer becomes 0.087-fold in terms of COS (85°) as compared with the vertical incidence. Namely, since the dust detection sensitivity becomes approximately 11-fold, the detection of dust smaller than a pixel of a camera becomes possible. In the macroscopic inspection for imaging the overall wafer, the size of the pixel of the camera tends to be relatively large, and the effect of improvement of this detection sensitivity is large in the detection of a defect of dust smaller than the size of the pixel.

Although a description has been given above of the angle of incidence of the illuminating light for improving the dust detection sensitivity, it is necessary to further attenuate the scattered light (diffracted light) due to the pattern incident upon the camera 11 for improving the scar detection sensitivity. Hereafter, a description will be given of this method separately concerning the positional relationship between the illuminating direction and the imaging direction and concerning the relationship in the width (angle) of a direction in which the diffracted light is absent.

(a) Positional Relationship Between Illuminating Direction and Imaging Direction When periodicity is present in the pattern, the scattered rays of light interfere with each other. Hence, rays of light scattered in a particular direction strengthen each other (i.e., diffracted light appears), but rays of light scattered in the other directions weaken each other and become very small. Accordingly, if the camera 11 is arranged so as to avoid the diffracting direction by making use of this characteristic, it is possible to substantially attenuate the scattered light due to the pattern, so that it becomes possible to selectively and brightly image the scattered light due to a defect which does not cause interference. However, since the diffracting direction changes depending on the period of the pattern, the wavelength of illumination, and the illuminating direction with respect to the pattern, it is necessary to make adjustment of the illuminating direction (or the imaging direction) depending on the type of wafer. However, this involves time and trouble, and there is no guarantee that a satisfactory dark field can be obtained.

Therefore, in the invention, by setting the positional relationship between the illuminating direction and the imaging direction as follows, an attempt is made to obtain a satisfactory dark field image under common illuminating conditions without performing adjustment of the illuminating direction (or the imaging direction) for each type of wafer.

Figure 2:
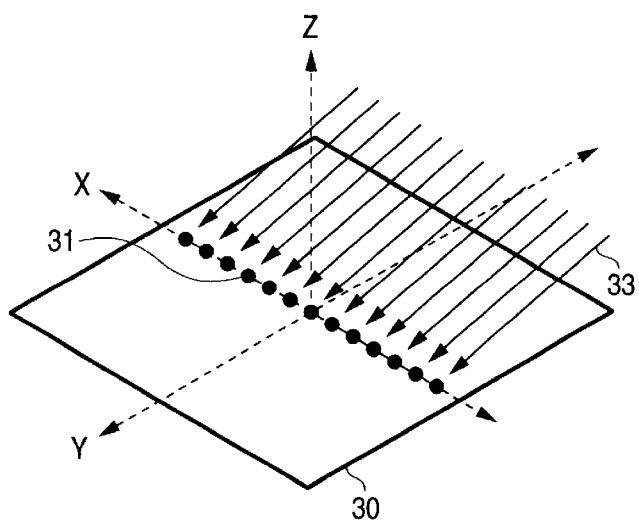
FIG. 2 is a diagram explaining a case in which a fine pattern is considered to be a row of dots arranged in a regular manner, and illumination is effected from a direction perpendicular to the periodic direction of the pattern.

Now, a diffraction pattern is examined in a case where, as shown in FIG. 2, it is assumed that a fine pattern consists of a row of dots 31 arranged in a regular manner, and that the illuminating light is ideal parallel rays of light and is applied from a direction perpendicular to the periodic direction of the pattern (it can be thought that a pattern formed on an actual wafer is formed by a multiplicity of such rows of dots 31 arranged continuously in a direction perpendicular to the periodic direction). It is assumed that the row of dots 31 constitutting the fine pattern is arranged on an X-Y orthogonal plane 30 at a period n along the X direction, and illuminating light 33 with a wavelength λ is applied in parallel from a Y direction perpendicular to the periodic direction of the row of dots 31. Further, it is assumed that the illuminating light 33 is applied to the surface of the plane 30 from a diagonal direction (from the direction at an angle of incidence θ with respect to the vertical direction of the plane 30, as described before). At this time, diffracted light occurs in the direction of arrangement of the row of dots 31 owing to the pattern of its periodic arrangement.

Figure 3:
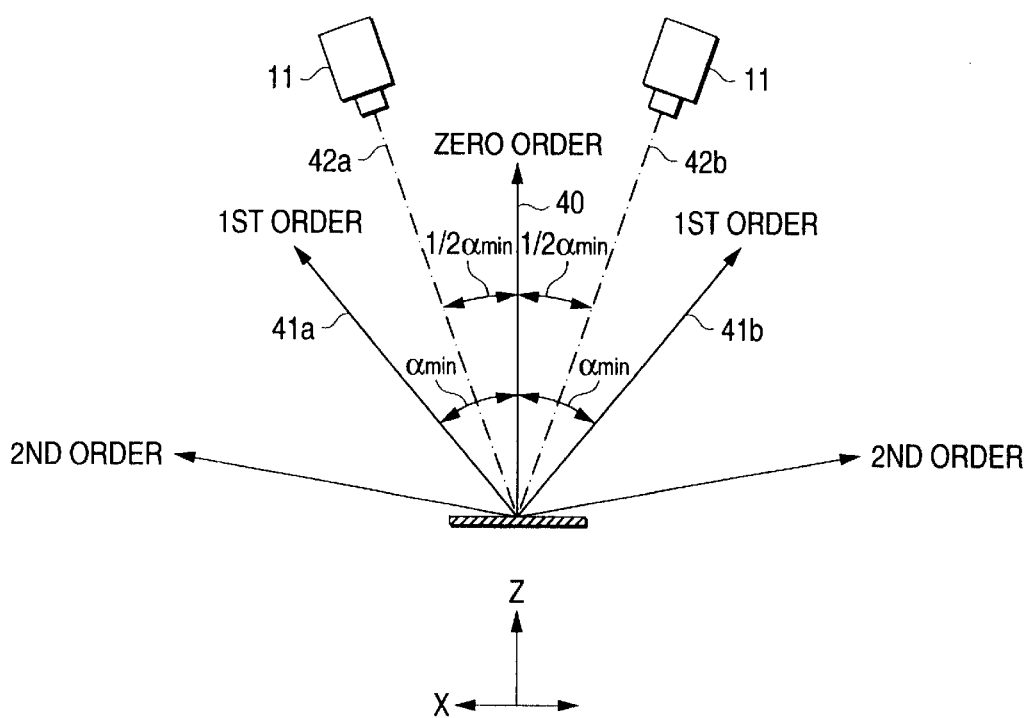
FIG. 3 is a diagram explaining the state of diffracted light in the illuminating direction shown in FIG. 2.

FIG. 3 is a diagram explaining the state of this diffracted light, and schematically shows the state of diffracted light when a cross section including the X axis is viewed (since the diffracted light due to the row of dots 31 is equivalent to a rotation with its direction of arrangement set as an axis, the state of diffracted light can be considered to be identical in any cross section insofar as it is a cross section including the X axis). The zero-order diffracted light due to the row of dots 31 of the fine pattern appears in such a manner as to be directed in the Z direction which is perpendicular to the plane 30. The diffracted light of orders other than the zero order changes and appears in various directions depending on the wavelength λ of the illuminating light and the period n of the row of dots 31. However, a direction in which diffracted light is not produced appears between the direction 40 of the zero-order diffracted light and the direction 41a (or direction 41b) of the 1st-order diffracted light which is formed at a minimum diffraction angle αmin. The minimum diffraction angle αmin can be determined by a maximum period n(max) of patters of different types and a shortest wavelength γ (min) among the illumination wavelengths used. Accordingly, if imaging is effected from a direction between the direction 40 of the zero-order diffracted light and the direction 41a (or direction 41b) of the 1st-order diffracted light, images in which the effect of diffracted light is minimized can be always obtained even if the type of pattern is different. Imaging is preferably effected from a direction 42a (or direction 42b) intermediate between the direction 40 of the zero-order diffracted light and the direction 41a (or direction 41b) of the 1st-order diffracted light.

It should be noted that if the aforementioned condition (the direction between the direction of the zero-order diffracted light and the direction of the 1st-order diffracted light) in the cross section including the X axis can be satisfied, it can be said that whatever imaging angles with respect to the Y direction are under the same condition. However, in obtaining a focused and undistorted image, it is preferable to effect imaging from a substantially perpendicular direction (Z direction) with respect to the wafer.

Figure 4:
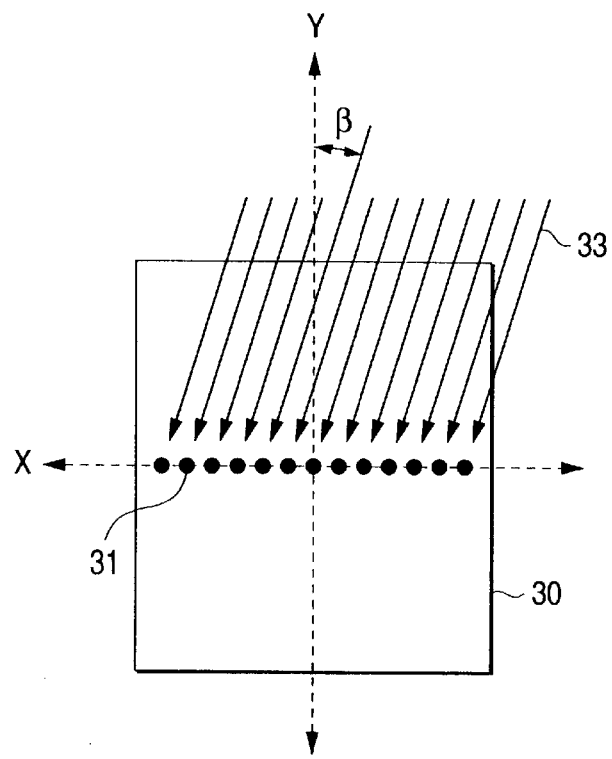
FIG. 4 is a diagram explaining a case in which the illuminating direction is tilted with respect to the direction perpendicular to the pattern.
Figure 5:
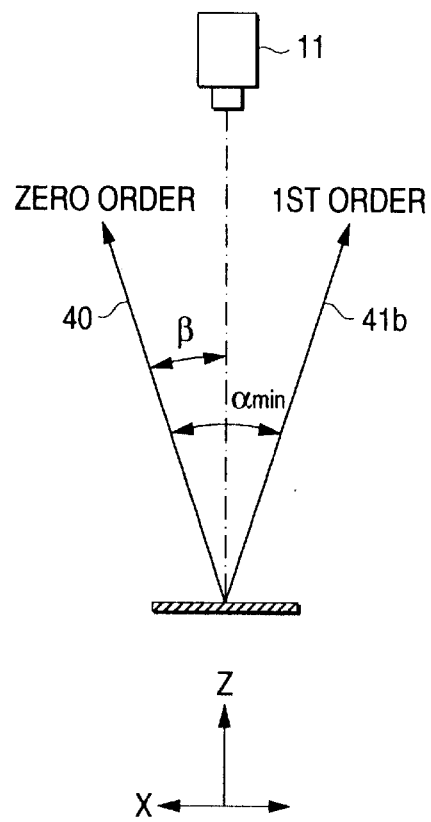
FIG. 5 is a diagram explaining the state of diffracted light in the illuminating direction shown in FIG. 4.

For example, the setting of the imaging direction 42b to the Z direction in FIG. 3 becomes possible by tilting the illuminating direction with respect to a direction perpendicular to the periodic direction of the pattern (it suffices if the illuminating direction is relatively offset). Namely, as shown in FIG. 4, if the illuminating light 33 is applied from a direction in which the illuminating light 33 is tilted by an angle β with respect to the Y direction, the zero-order diffracted light is tilted by the same angle β as the inclination of the illuminating light with respect to the Z direction (see FIG. 5 which schematically shows the state of diffracted light when a cross section including the X axis is viewed in the same way as FIG. 3). Accordingly, if the imaging direction is set intermediate between the directions of the zero-order and the 1st-order diffracted light, it suffices if β=αmin ·½.

(b) Relationship of the Width of the Direction in Which Diffracted Light is Absent To obtain an image in which the scattered light (diffracted light) is attenuated, the width of the direction in which the diffracted light is absent has a further bearing, so that a description will be given of this aspect.

Even if the positional relationship between the imaging direction and the illuminating direction is set under the aforementioned condition, if the imaging lens of the camera 11 is made excessively large (i.e., if the aperture angle of the imaging lens is excessively large), the diffracted light is incident upon the camera 11, so that a sufficient dark field state cannot necessarily be obtained.

Further, as for the illuminating light, ideal parallel rays of light can be formed if laser light is used, but the quantity of light as the dark field illumination is small, so that the laser light is not necessarily suitable for use. In the case of a general halogen lamp, the quantity of light as the dark field illumination is sufficient; however, completely parallel rays of light cannot be obtained even if a collimator lens is used, so that diversion occurs in the direction of diffracted light. If this diffracted light is too large, the diffracted light is still incident upon the camera 11, so that a sufficient dark field state cannot necessarily be obtained.

Figure 6:
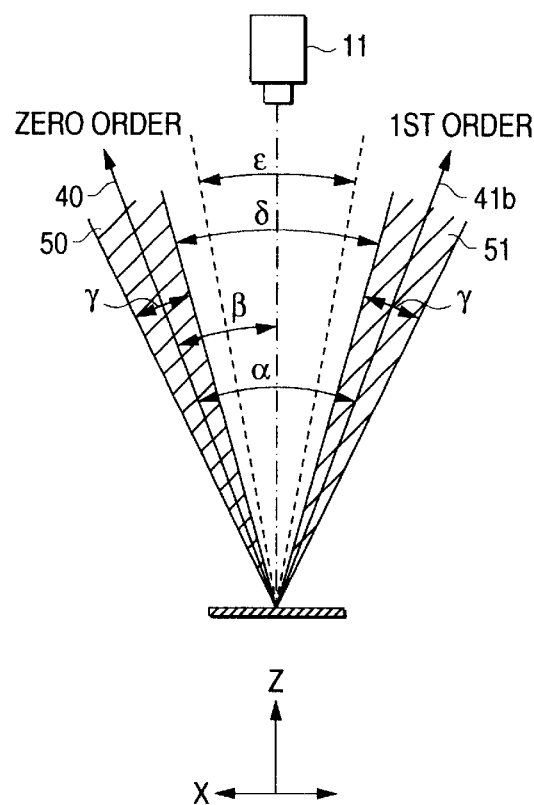
FIG. 6 is a diagram explaining the relationship of the width in a direction in which diffracted light is absent.

Referring to FIG. 6, a description will be given of the relationship of the width of the direction in which the diffracted light is absent. In FIG. 6, the direction 40 of the zero-order diffracted light is tilted by the same angle $\beta$ as the inclination of the illuminating light with respect to the Z direction, and the angle $\beta$ is set to ½ of the diffraction angle $\alpha$. Further, it is assumed that imaging is effected from the Z direction.

Figure 7:
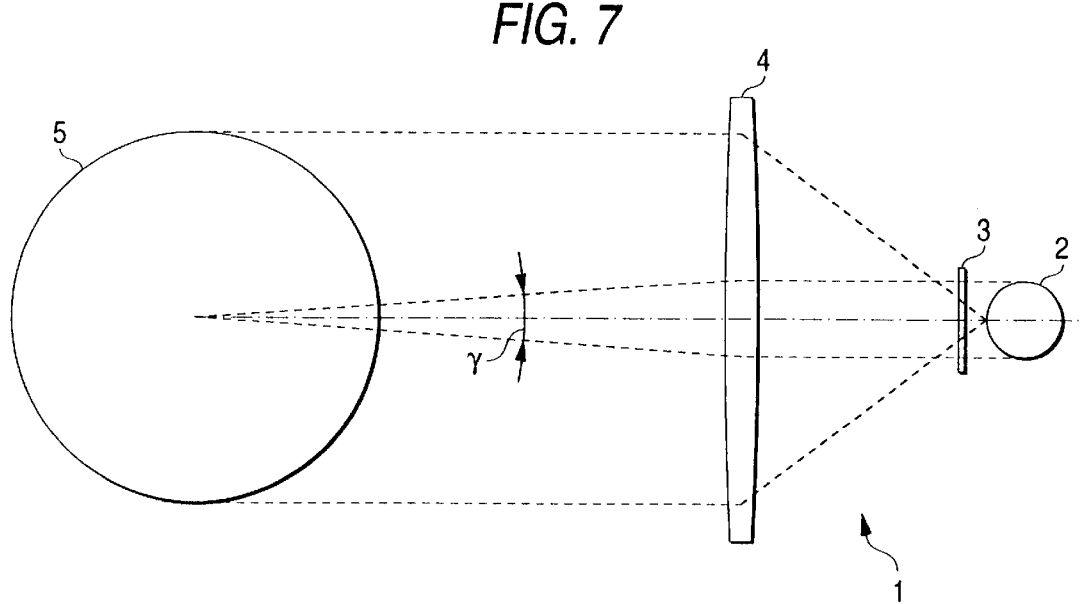
FIG. 7 is a diagram illustrating the aperture angle $\gamma$ of the dark field illuminating light in a direction parallel to the wafer surface.

Here, if the illuminating light is not completely parallel, the zero-order diffracted light and the 1st-order diffracted light assume widths (angles), as indicated by shaded regions 50 and 51, respectively. These widths (angles) become identical to the aperture angle $\gamma$ of the dark field illumination in a direction parallel to the wafer surface (see FIG. 7). Namely, diffracted light is made incident if the width of the imaging lens is larger than the width (angle $\sigma$) in which ½ portions of the respective aperture angles $\gamma$ are inwardly subtracted from an angle formed by the direction 40 of the zero-order diffracted light and the direction 41b of the 1st-order diffracted light when the illuminating light is made completely parallel light. Conversely speaking, if imaging is effected with an angular width smaller than this angle $\sigma$, it is possible to obtain an image which is not affected by the diffracted light.

Figure 8:
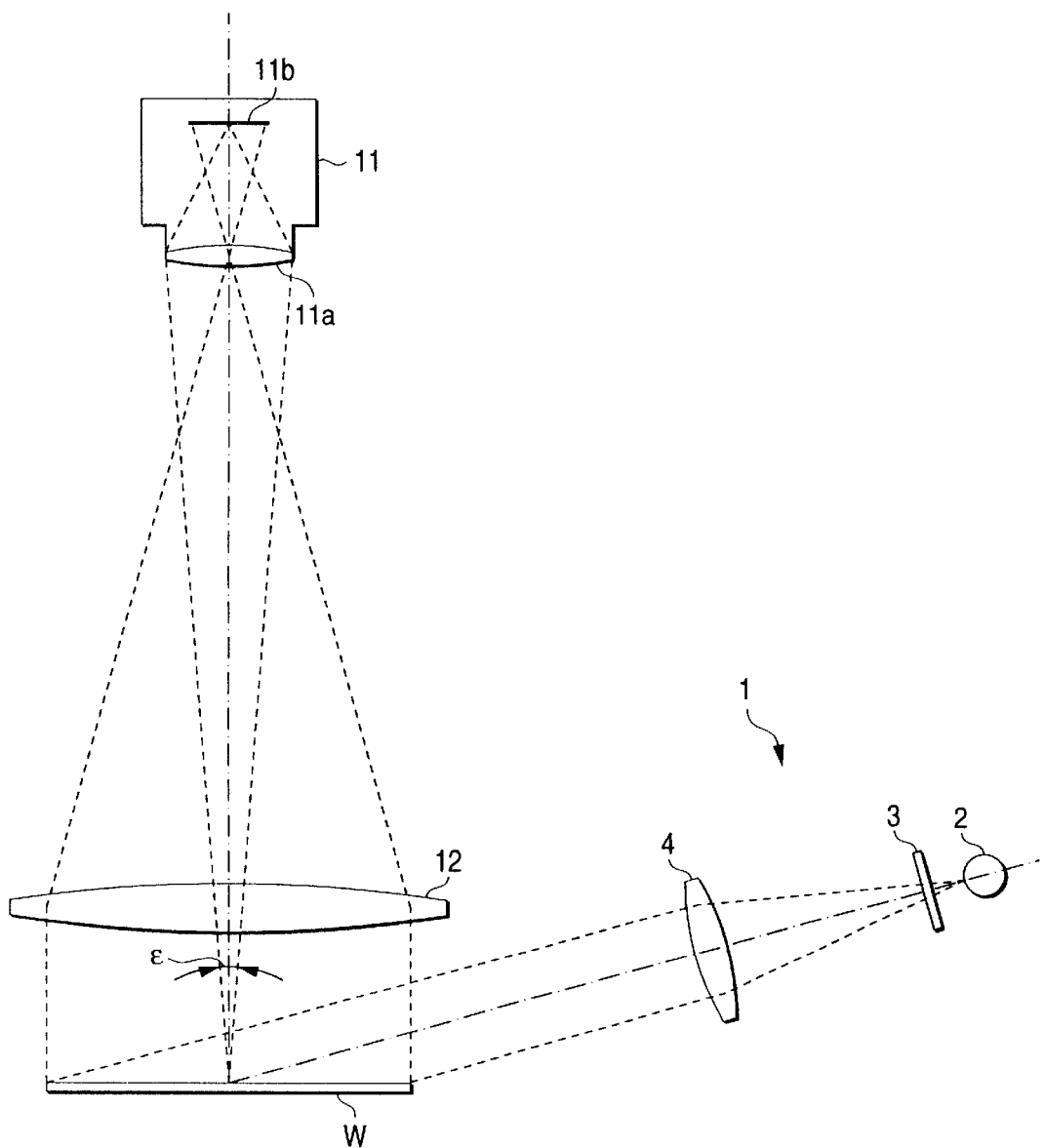
FIG. 8 is a diagram illustrating the aperture angle $\epsilon$ of an imaging lens on the side of an object to be inspected.

In addition, in a case where the imaging direction is set intermediate between the direction 40 of the zero-order diffracted light and the direction 41b of the 1st-order diffracted light, if the aperture angle $\epsilon$ of an imaging lens 11a of the camera 11 on the side of the object to be inspected is made smaller than the angle $\sigma$, the diffracted light ceases to be incident upon an imaging element surface 11b, as shown in FIG. 8.

To sum up the foregoing, necessary conditions for attenuating the scattered light incident upon the camera 11 are as follows.

aperture angle $\epsilon$ of the imaging lens+aperture angle $\gamma$ of illuminating light<width (angle) in a direction in which diffracted light is absent=diffraction angle $\alpha$ Further, if it is assumed that the illumination wavelength used is $\lambda$, and the period of the pattern is n, the diffraction angle $\alpha$ can be determined by:

$\alpha = \sin^{-1}(\lambda/n)$

It should be noted that although the imaging direction is preferably intermediate between the direction of the zero-order diffracted light and the direction of the 1st-order diffracted light, the imaging direction may be slightly offset to either direction insofar as the total of the aperture angle $\epsilon$ of the imaging lens and the aperture angle $\gamma$ of the dark field illuminating light is sufficiently smaller than the diffraction angle $\alpha$.

From the foregoing, in a case where patterns of different types are inspected, since the minimum diffraction angle $\alpha$min is determined by a maximum period n(max) of the pattern and the shortest wavelength $\lambda$ (min) of the illuminating light based on the narrow-band pass filter 3, the aperture angle $\epsilon$ of the imaging lens and the aperture angle $\gamma$ of the illuminating light are set in correspondence therewith, it becomes possible to obtain dark field images constantly even if the patterns are of different types.

Incidentally, among the patterns on the wafers, very fine patterns such as memory cells and large dot-like patterns for connection to external lead wires are potentially present in mixed form. Hence, if the diffraction angle is calculated for the large patterns, the value becomes extremely small. However, regular reflection (zero-order diffracted light) is the mainstream in such a large pattern, and practically no scattered light (higher-order diffracted light) occurs. Therefore, satisfactory dark field images can be obtained even if the diffraction angle is not taken into consideration. Those patterns for which the diffraction angle needs to be taken into consideration are very fine patterns having sizes up to several times as large as the wavelength used.

Next, a brief description will be given of the operation of defect inspection in accordance with the embodiment shown in FIG. 1. First, the wafer W is placed on the X-Y stage 5. At this time, the periodic direction of the pattern of the wafer W is placed in such a positional relationship as to conform with the direction parallel to the X direction of the X-Y stage 5. Incidentally, the optical system 1 for dark field illumination and the imaging optical system 10 are arranged in the positional relationship described with reference to FIGS. 4 and 5, while the camera 11 is set in a substantially perpendicular direction (Z direction) to the wafer W. Meanwhile, the illuminating direction of the optical system 1 for dark field illumination is set so as to be tilted by the angle $\beta$ with respect to the Y direction of the X-Y stage 5.

The wafer W subjected to dark field illumination by the optical system 1 for dark field illumination is imaged by the camera 11. At this time, since the diffracted light due to a fine pattern is attenuated, a dark field image which is dark can be obtained. The image signal from the camera 11 is fetched into the image processor 20, and is stored in its memory 20a. The image processor 20 effects defect inspection on the basis of the stored dark field image. If there is a defect such as a scar or dust is present on the wafer, the luminance of the scattered light from the defect is relatively high as compared with a dark field image other than the defect, the defect is detected by comparing the luminance with a threshold.

The method of inspecting a defect by dark field illumination from one direction has been described above. However, among the patterns on the wafers, a portion having periodicity in a vertical direction and a portion having periodicity in a horizontal direction are potentially present in mixed form. In that case, there is a possibility that a single image based on dark field illumination from one direction cannot provide a best dark field image.

In addition, in the case of patterns which do not have perfect periodicity such as logic ICs or system LSIs in which various types of circuits are integrated on single chips, some portions become bright even if dark field illumination is effected from any direction. In this case, there is a possibility that a satisfactory dark field image cannot be obtained.

Figure 9:
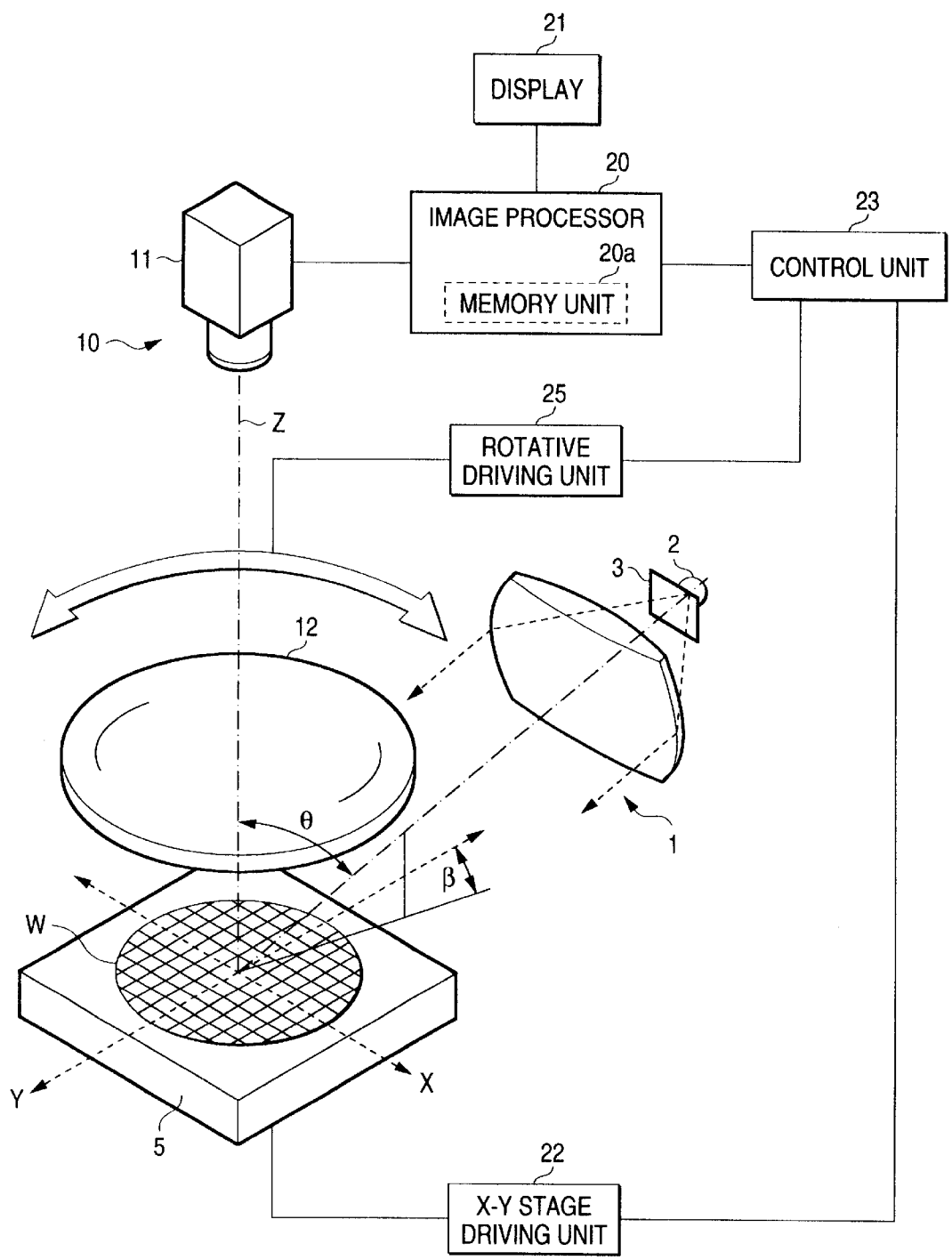
FIG. 9 is a diagram illustrating the configuration of a defect inspecting apparatus in accordance with a modification.

Referring to FIG. 9, a description will be given of a modification of a defect inspecting apparatus for such a pattern. The defect inspecting apparatus shown in FIG. 9 has an arrangement in which a rotatively driving unit 25 for rotating the optical system 1 for dark field illumination with the vertical axis (Z axis) of the X-Y stage 5 as a center of rotation is added to the apparatus shown in FIG. 1. The other arrangements are similar to those of FIG. 1. The driving of the rotation of the optical system 1 for dark field illumination by the rotatively driving unit 25 is controlled by a control unit 23.

Figure 10:
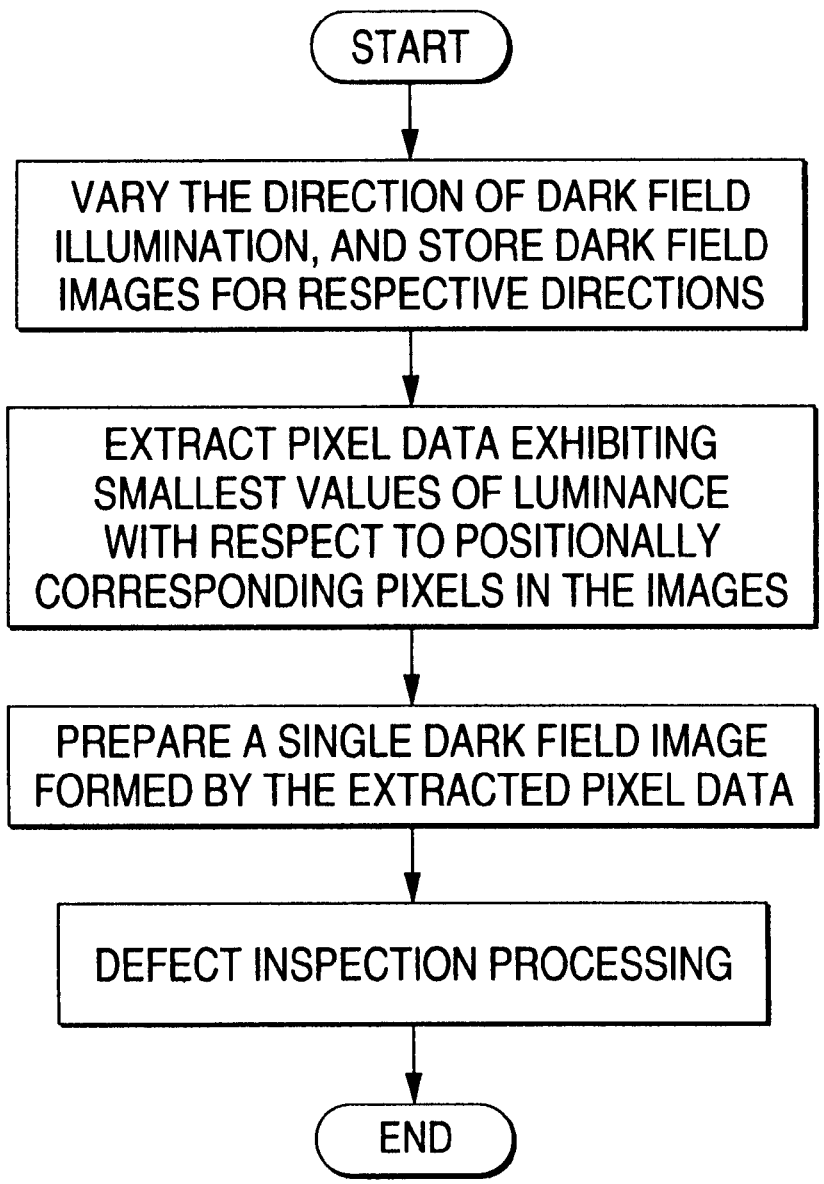
FIG. 10 is a diagram illustrating a flowchart of inspection in the defect inspecting apparatus in accordance with the modification.

A description will be given of defect inspection by this apparatus (see the flowchart shown in FIG. 10). First, the wafer W is illuminated by the optical system 1 for dark field illumination placed at a predetermined rotating position, a first image is picked up, and the image processor 20 stores it in its memory 20a. Next, the control unit 23 drives the rotatively driving unit 25 to rotate the illuminating optical system 1 through each fixed angle, and dark field images of the wafer W which are picked up by the camera 11 in synchronism with the rotation are consecutively stored in the memory 20a.

When a plurality of images have been obtained after rotating the illuminating optical system 1 up to a predetermined angle (e.g., 90 degrees from a predetermined position), the image processor 20 extracts darkest pixels (pixels exhibiting minimum values of luminance) among positionally corresponding pixels (pixels at the same positions) in the respective image data. The image processor 20 then prepares a single dark field image formed by the extracted pixel data at the respective positions. This processing may be effected concurrently with the fetching of the images.

If the illuminating direction is rotated, the various circuits on one chip respectively repeat light and dark at different periods, and all the circuits do not become dark simultaneously, but if the pixels which became darkest are collected, a satisfactory dark field image can be obtained. The image processor 20 effects detection of a defect such as a scar or dust by processing the prepared image. Consequently, even in the case of a logic IC or a system LSI, a satisfactory dark field image can be obtained, and the defect detection can be performed with high sensitivity.

It should be noted that in a case where scanning is effected by rotating the illuminating direction, higher-order diffracted light passes through the periphery of the imaging lens of the camera 11. Since the higher-order diffracted light has a spread corresponding to the band of the illumination wavelength, it is preferable to narrow down the bandwidth of the illuminating light so as to obtain a satisfactory dark field image. In this embodiment, this is realized by using the narrow-band pass filter 3. The wavelength based on the filter 3 and the width of its narrow band are designed in correspondence with the spectrum distribution of the quantity of light of the light source 2 and the detection sensitivity on the camera 11 side.

In addition, as for the rotation of the optical system 1 for dark field illumination in the above description, it suffices if its rotational angle is determined in correspondence with the type of pattern, and the number of pieces of image data to be stored may be set from such as the relationship between the processing time and the detection accuracy depending on the type of pattern.

Figure 11:
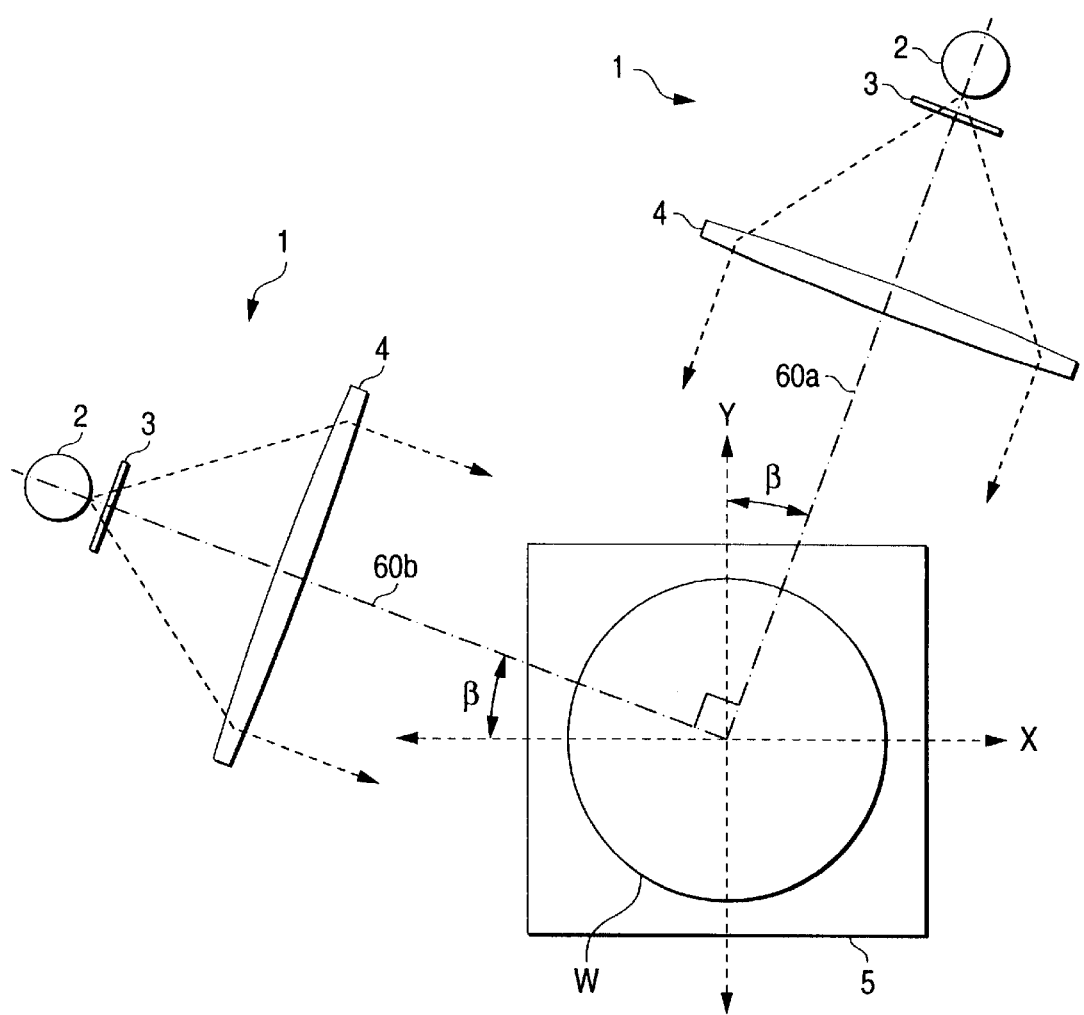
FIG. 11 is a diagram illustrating an example in which optical systems for dark field illumination are arranged in at least two directions.

In the case of the wafer W in which patterns having periodicity in mutually perpendicular directions such as the vertical direction and the horizontal direction are present in mixed form, it suffices if the same processing as described above is effected by obtaining respective images from at least two directions, as described below. Namely, as shown in FIG. 11, the optical system 1 for dark field illumination is disposed so as to be able to effect illumination from a first direction 60a tilted by the angle β, which is determined in the above-described manner, with respect to the Y direction of the X-Y stage 5 and from a second direction 60b perpendicular to the direction 60a. This arrangement can be provided by changing the illuminating direction of the optical system 1 for dark field illumination by the rotatively driving unit 25, or by preparing two optical systems 1 for dark field illumination and fixedly arranging them in the respective directions 60a and 60b. Then, the wafer W is disposed such that the vertical and horizontal periods of the patterns are parallel to the X direction and the Y direction of the X-Y stage 5.

In the dark field illumination from the direction 60a, an image can be obtained in which the diffracted light of the pattern having a periodic direction perpendicular to the Y direction is attenuated. In the dark field illumination from the direction 60b, an image can be obtained in which the diffracted light of the pattern having a periodic direction perpendicular to the X direction is attenuated. On the basis of these two items of image data, positionally corresponding pixels exhibiting relatively smaller luminance, as described above, are extracted, and a single dark field image formed by the extracted pixel data at the respective positions is prepared, thereby making it possible to effect defect detection easily with high sensitivity.

It should be noted that although, in the embodiment shown in FIG. 9, the optical system 1 for dark field illumination is arranged to be rotated with respect to the wafer W, it is possible to obtain a relatively identical relationship if the X-Y stage 5 for placing the wafer W thereon and the imaging optical system 10 are rotated about the Z axis.

As described above, in accordance with the present invention, it is possible to effect defect inspection easily with high sensitivity without performing complicated adjustment or processing in dark field illumination even with respect to objects to be inspected having different types of periodic patterns.

What is claimed is:

1. A defect inspecting apparatus for macroscopically inspecting a defect of an object having a periodic fine pattern, said apparatus comprising:

a dark field illumination optical system that illuminates a region of the object with substantially parallel illumination light in a direction having a predetermined first inclined angle relative to an inspection surface of the object, the region being larger than a size of one fine pattern;

an imaging optical system that images the region of the object illuminated with the illumination light, the imaging optical system having an imaging lens and an imaging element having a lower resolution in comparison to the fine pattern imaged by the imaging lens; and defect detecting means that detects the defect by processing image data thus imaged;

wherein an optical axis direction of the imaging optical system is set between a direction of zero-order diffraction light of the illumination light and a direction of $1^{st}$-order diffraction light that is formed, with respect to the direction of the zero-order diffraction light, at a minimal diffraction angle α min defined by a maximum period n (max) of the fine pattern to be inspected and a minimal wavelength λ (min) of the illumination light; and wherein a sum of an aperture angle γ of the illumination light and an aperture angle ε of the imaging lens is set to be smaller than a diffraction angle α.

2. A defect inspecting apparatus of claim 1, wherein the optical axis direction of the imaging optical system is set substantially in the middle between the direction of the zero-order diffraction light and the direction of the 1st-order diffraction light.

3. A defect inspecting apparatus of claim 1, wherein an optical axis direction of the illumination optical system is set to have the predetermined first inclined angle relative to an inspection surface of the object region and to perpendicularly intersect a periodic direction of the fine pattern.

4. A defect inspecting apparatus of claim 1, wherein:
the optical axis direction of the imaging optical system is set to be substantially perpendicular to an inspection surface of the object region; and
an optical axis direction of the illumination optical system is set to have the predetermined first inclined angle relative to the inspection surface of the object region and a predetermined second inclined angle to a direction perpendicularly intersecting a periodic direction of the fine pattern.

5. A defect inspecting apparatus of claim 1, wherein the second inclined angle is substantially identical to an angle defined between the direction of the zero-order diffraction light or the 1st order diffraction light and the optical axis direction of the imaging optical system.

6. A defect inspecting apparatus of claim 1, further comprising:
means for mutually varying an optical axis direction of the illumination optical system;
image preparing means for extracting pixel data of a smallest luminance from data of positionally identical pixels on images taken each time when the optical axis direction of the illumination optical system is varied, and preparing image data from the extracted pixel data,
wherein the defect detecting means detects the defect based on the thus prepared image data.

7. A defect inspecting apparatus, for macroscopically inspecting a defect of an object having a periodic fine pattern, said apparatus comprising:
a dark field illumination optical system that illuminates the object with substantially parallel illumination light in a direction having a predetermined inclined angle relative to an inspection surface of the object;
an imaging optical system that images the object illuminated with the illumination light, the imaging optical system having an imaging lens and an imaging element;
means for mutually varying an optical axis direction of the illumination optical system, the varying means including first rotating means for rotating the illumination optical system relative to the object or second rotating means for rotating the object and the imaging optical system;
image preparing means for extracting pixel data of a smallest luminance from data of positionally identical pixels on images taken each time when the optical axis direction of the illumination optical system is varied, and preparing image data from the extracted pixel data; and
defect detecting means for detecting the defect based on the thus prepared image data;
wherein a mutual positional relationship between the optical axis direction of the illumination optical system and an optical axis direction of the imaging optical system is determined based on a diffraction angle α defined by a period n of the fine pattern and a wavelength λ of the illumination light.

8. A defect inspecting apparatus of claim 7, wherein the dark field illumination optical system or the imaging optical system has means for setting a wavelength band to a narrow band.

9. A defect inspecting apparatus for macroscopically inspecting a defect of an object having a periodic fine pattern, said apparatus comprising:
a dark field illumination optical system that illuminates the object with substantially parallel illumination light in a direction having a predetermined inclined angle relative to an inspection surface of the object;
an imaging optical system that images the object illuminated with the illumination light, the imaging optical system having an imaging lens and an imaging element;
means for mutually varying an optical axis direction of the illumination optical system, the varying means including first rotating means for rotating the illumination optical system relative to the object or second rotating means for rotating the object and the imaging optical system;
image preparing means for extracting pixel data of a smallest luminance from data of positionally identical pixels on images taken each time when the optical axis direction of the illumination optical system is varied, and preparing image data from the extracted pixel data; and
defect detecting means for detecting the defect based on the thus prepared image data;
wherein a sum of an aperture angle γ of the illumination light and an aperture angle α of the imaging lens is set to be smaller than a diffraction angle α.

10. A defect inspecting apparatus of claim 9, wherein the dark field illumination optical system or the imaging optical system has means for setting a wavelength band to a narrow band.

* * * * *